United States Patent [19]

Papenfuhs et al.

[11] Patent Number: 4,760,183
[45] Date of Patent: Jul. 26, 1988

[54] PROCESS FOR THE PREPARATION OF AROMATIC DIALKYLAMINES

[75] Inventors: Theodor Papenfuhs; Walter Kühn, both of Frankfurt am Main, Fed. Rep. of Germany

[73] Assignee: Hoechst Aktiengesellschaft, Frankfurt am Main, Fed. Rep. of Germany

[21] Appl. No.: 893,362

[22] Filed: Aug. 5, 1986

[30] Foreign Application Priority Data

Aug. 7, 1985 [DE] Fed. Rep. of Germany ....... 3528262

[51] Int. Cl.$^4$ .............................................. C07C 85/08
[52] U.S. Cl. ..................... 564/398; 564/86; 564/177; 564/180; 564/184; 564/218; 260/508; 558/56; 560/43; 562/433
[58] Field of Search ................. 564/86, 177, 186, 184, 564/218, 398; 260/508; 558/56; 560/43; 562/433

[56] References Cited

U.S. PATENT DOCUMENTS

| 2,947,784 | 8/1960 | Martin et al. | 564/398 |
| 3,336,386 | 8/1967 | Dovell et al. | 564/398 |
| 3,522,309 | 7/1970 | Kirby | 564/398 |

FOREIGN PATENT DOCUMENTS

832296 2/1976 Belgium .

OTHER PUBLICATIONS

*Hackh's Chemical Dictionary*, Grant, J., Ed., McGraw-Hill Book Co., New York (1983).
Möller et al, "Amines via Reduction", in Houben-Weyl, 11/1, Georg Thieme Verlag. Stuttgart, 1957, pp. 642–645.
Pearson et al, J. Amer. Chem. Soc. 73, 864 (1951).
Emerson et al, J. Amer. Chem. Soc. 63, 749–51 (1941).
Stühmer et al, Ber. der Deut. Chem. Ges. 83, 66–68 (1950).
Emerson, "The Preparation of Amines . . . ", Ch. 3 in: *Organic Reactions,* vol. IV, John Wiley & Son, N.Y., pp. 174–255.

*Primary Examiner*—Glennon H. Hollrah
*Assistant Examiner*—John A. Sopp

[57] ABSTRACT

A process for the preparation of aromatic dialkylamines of the formula (1)

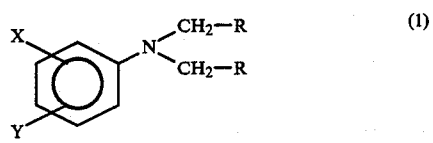

in which R denotes an alkyl-$C_1$-$C_6$ group, X and Y each denote a hydrogen, fluorine or chlorine atom or a hydroxyl, alkyl-$C_1$-$C_4$, alkoxy-$C_1$-$C_4$, carboxyl, carbalkoxy-$C_1$-$C_5$, alkyl-$C_1$-$C_4$—CO—NH—,

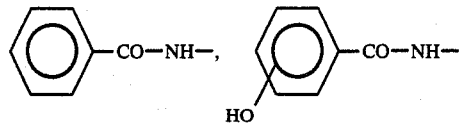
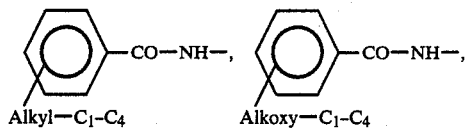
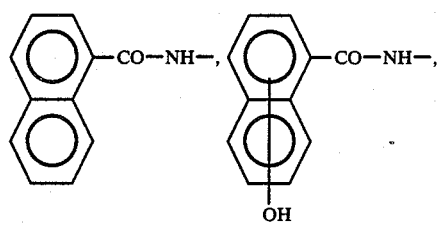
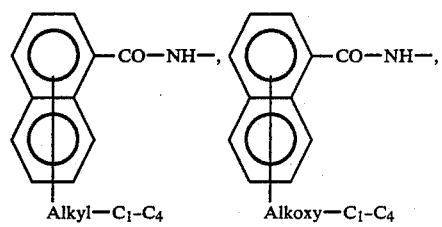
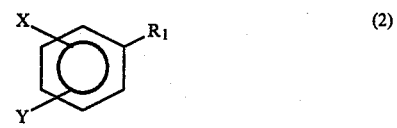

sulfonic acid, alkyl-$C_1$-$C_4$ sulfonate, sulfamoyl, alkyl-$C_1$-$C_4$-sulfonyl, hydroxy-alkylene-$C_1$-$C_4$-sulfonyl, phenylsulfonyl, hydroxyphenylsulfonyl, alkyl-$C_1$-$C_4$-phenylsulfonyl or alkoxy-$C_1$-$C_4$-phenylsulfonyl group, wherein compounds of the formula (2)

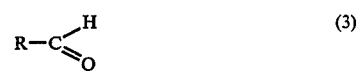

in which $R_1$ denotes a nitro or primary amino group, and X and Y have the mentioned meanings, are reductively dialkylated using at least equimolar amounts of an aldehyde of the formula (3)

$$R-C\overset{H}{\underset{O}{\lessgtr}} \qquad (3)$$

in which R has the abovementioned meaning, in alcohols, alkylbenzenes, glycol ethers, fatty acid dialkylamides or fatty acid alkyl esters or fatty acid glycol esters, and using catalytically activated hydrogen in the presence of a precious metal catalyst of group 8 of the periodic table, if appropriate in the presence of catalytic amounts of a trialkyl-$C_1$-$C_6$-amine, at 50° C. to 150° C. at a pressure of 20 bar to 100 bar.

5 Claims, No Drawings

PROCESS FOR THE PREPARATION OF AROMATIC DIALKYLAMINES

The invention relates to a process, which is improved regarding industrial hygiene, ecology and yield, for the preparation of aromatic dialkylamines, which have great importance as coupling components for the preparation of disperse azo dyes and for the synthesis of cationic dyes.

The industrial preparation of aromatic dialkylamines of the general formula (1)

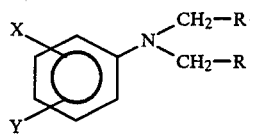

in which R denotes an alkyl-$C_1$-$C_6$ group, X and Y each denote a hydrogen, fluorine or chlorine atom or a hydroxyl, alkyl-$C_1$-$C_4$, alkoxy-$C_1$-$C_4$, carboxyl, carbalkoxy-$C_1$-$C_5$, Alkyl-$C_1$-$C_4$-CO—NH—,

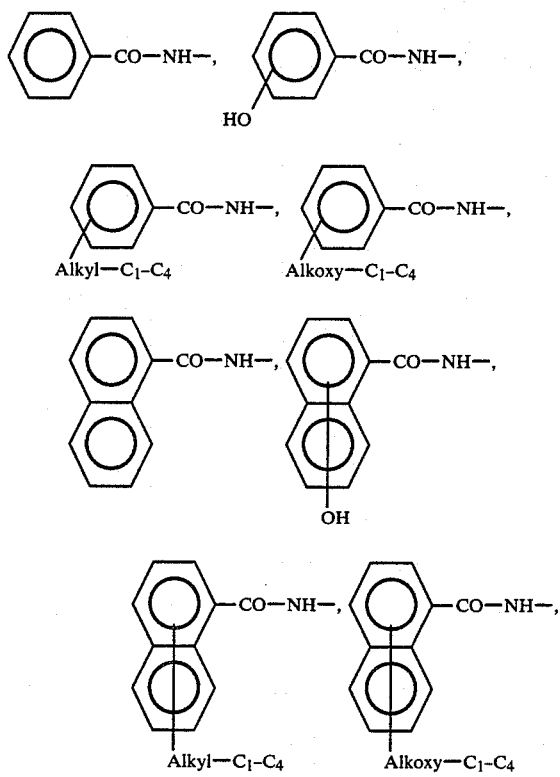

sulfonic acid, alkyl-$C_1$-$C_4$ sulfonate, sulfamoyl, alkyl-$C_1$-$C_4$-sulfonyl, hydroxy-alkylene-$C_1$-$C_4$-sulfonyl, phenylsulfonyl, hydroxyphenylsulfonyl, alkyl-$C_1$-$C_4$–phenylsulfonyl or alkoxy-$C_1$-$C_4$-phenylsulfonyl group, has hitherto generally been carried out from the base nitro compounds of the general formula (2) (see below), which are reduced to the corresponding amino compounds of the formula (3) and are subsequently reacted with an alkylating agent of the general formula R—CH$_2$—Z, in which R has the abovementioned meaning and Z denotes a chlorine or bromine atom or the —OSO$_2$—OCH$_2$—R group (R here again has the abovementioned meaning), such as alkyl halides or alkyl sulfates, in the presence of stoichiometric amounts of an acid acceptor to form the target compounds of the mentioned formula (1) according to the reaction scheme

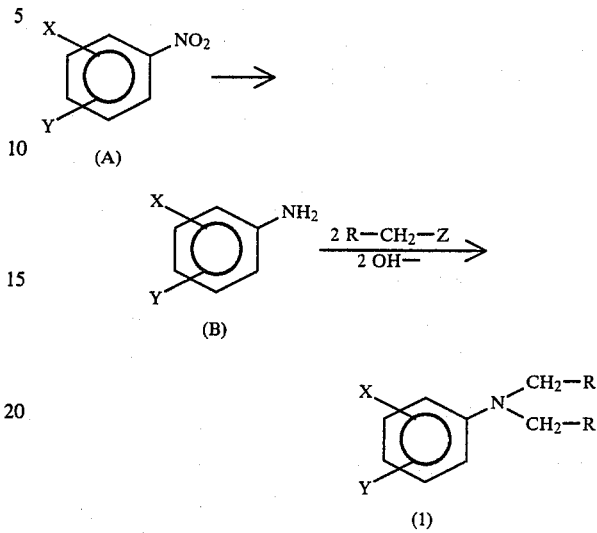

These process steps are, however, not ideal from the industrial hygiene, ecological and economic points of view, since (1) the alkylating agents of the mentioned general formula R—CH$_2$—Z (one of the starting compounds) are physiologically questionable, (2) the alkylating agent must be used in excess, (3) it is scarcely possible to avoid formation of ethers as a side reaction, (4) a high salt pollution of the waste waters with sodium chloride/sodium sulfate and with organic compounds (alkanols from the excesses (cf. point 2)) is caused, (5) losses in yield by quaternization (combined with further waste water pollution) must be accepted, (6) low selectivity usually results, and (7) the amine (B) (starting compound) to be alkylated must be prepared from the nitro compound (A) in separate reaction steps.

There was, therefore, a demand for a more favorable process, avoiding the mentioned disadvantages, for the preparation of aromatic dialkylamines. The reductive alkylation, which is known in principle, of aromatic nitro or amino compounds using carbonyl compounds was examined in greater detail during the search for a suitable solution. In this case, however, it was found that, according to the state of the art, dialkylation in the wider sense, of necessity limited to dimethylation, is only possible when formaldehyde is used as the carbonyl compound, and variable yields are obtained depending on the nitro or amino compound to be alkylated [HOUBEN-WEYL 11/1, page 642. et. seq.] In this case, however, acceptable results regarding yield and product quality can at best be achieved, such as by means of reductive dimethylation in corrosive acidic medium, under conditions which can only be fulfilled with difficulty [JACS 73, 864 (1951); Belgian Patent Specification No. 832,296].

In contrast, the reductive dialkylation of aromatic nitro or amino compounds using higher aldehydes of the formula

in which R has the abovementioned meaning, is, according to the literature, if mentioned there at all, only possible under technically impracticable conditions and with unsatisfactory yields. Thus, the dialkylanilines are obtained in a yield of 34–70% after 96 hours on reaction of nitrobenzene with aliphatic aldehydes of the formula

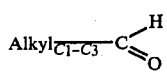

in glacial acetic acid/ethanol on $PtO_2$ on hydrogenation under standard pressure [JACS 63, 749 (1941)].

Similarly, the reductive diethylation of 1-amino-2-hydroxy-1,2-diphenylethane using acetaldehyde on $Pt/BaSO_4$ only succeeds in the presence of aluminum chloride in 50% yield. In the absence of aluminum chloride, the monoethyl compound is produced almost exclusively [Ber. 83, 66 (1950)].

Surprisingly, it has now been found that, contrary to the prejudice caused by the cited literature references, aromatic dialkylamines of the abovementioned general formula (1) can be prepared in high yield and selectivity by reductively dialkylating compounds of the general formula (2)

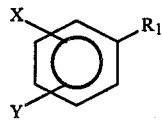

in which $R_1$ denotes a nitro or primary amino group and X and Y have the abovementioned meanings, using at least equimolar amounts of an aldehyde of the general formula (3)

in which R has the abovementioned meaning, in alcohols, such as alkanols ($C_1$–$C_6$), for example methanol, ethanol, isomeric propanols, butanols or their higher homologs; alkylbenzenes, such as toluene, ethylbenzene or isomeric xylenes, or mixtures thereof; glycol ethers, such as, for example, methyl, ethyl or butyl glycol, methyl, ethyl or butyl diglycol, methyl, ethyl or butyl triglycol or methyl, ethyl or butyl tetraglycol; fatty acid dialkylamides, such as, for example, dimethyl formamide; or, preferably, in fatty acid alkyl esters or fatty acid glycol esters, such as, for example, the methyl, ethyl, butyl or glycol esters of acetic acid, propionic acid or butyric acid, and using catalytically activated hydrogen in the presence of a precious metal catalyst from group 8 of the periodic table, for example platinum or, particulary, palladium, preferably on a suitable carrier material (charcoal or barium sulfate), furthermore modified platinum catalysts, such as platinum dioxide or sulfided or sulfited platinum, the catalyst being employed expediently in an amount from 1 to 20 g/mol, preferably from 5 to 10 g/mol, referred to the starting compound of the mentioned formula (2), if appropriate in the presence of catalytic amounts of a trialkyl-$C_1$-$C_6$-amine, such as, for example, triethylamine or tributylamine, in an amount from 1 to 20 mol-%, preferably 5 to 10 mol-%, relative to the starting compound of the mentioned formula (2), at temperatures from 50° C. to 150° C., preferably 80° C. to 120° C., at a pressure from 20 bar to 100 bar, preferably 40 bar to 60 bar.

Whereas it is disadvantageous to carry out the process according to the invention in acidic medium, it has, surprisingly, often proven advantageous to work in basic medium. In the literature, only a selective monoaklylation has been described hitherto for work in basic medium (Organic Reactions 4, 174; Japanese Published Specification No. 57/123,148).

Notably, dimethylation of the starting compounds of the formula (2) using formaldehyde does not succeed under the conditions according to the invention, so that the smooth course of the reaction using the aldehydes of the mentioned formula (3) is extremely surprising and was in no way to be expected. The new process gives the aromatic dialkylamines (1) in excellent yields and very high selectivity (<1% of monoalkyl compound).

Since the addition of acid, solid auxiliaries, such as aluminum chloride or acidic polymers, and catalyst complexes is not necessary in the process according to the invention, it can be carried out in industrially ideal fashion in any hydrogenation apparatus, particularly in the hydrogenators which have been introduced in industry, for the production of aromatic amines from their nitro precursors. In addition, the abovementioned disadvantages of the industrial processes hitherto used for the preparation of aromatic dialkylamines can be avoided completely and the nitro compounds (formula (2)) with $R_1$=nitro can be converted directly to the aromatic dialkylamines in a one-pot reaction. The process according to the invention thus represents a very considerable technical advance.

In detail, the process is carried out by hydrogenating solutions of the amines or nitro compounds (formula (2)) using =2 moles of an aldehyde of the formula (3) in the stated solvents, if appropriate in the presence of catalytic amounts of tertiary amines, on the abovementioned catalysts until hydrogen take-up is complete.

The experimental conditions are here as follows: the amine or the nitro compound of the formula (2) is hydrogenated in the abovementioned solvents, preferably in n-butyl acetate, as a 10 to 50% strength solution (50% strength solutions for the amines and 20% strength solutions for the nitro compounds have proven particularly advantageous), if appropriate in the presence of catalytic amounts of tertiary amines, particularly 10 mol-% of triethylamine, relative to the starting compound to be reacted, using 2.0 to 10.0 moles, preferably 2.5 to 3.5 moles, of an aldehyde of the formula (3) at 70° C. to 120° C., preferably at 80° to 100° C., and 20 to 100 bar, preferably 40 to 60 bar, of hydrogen pressure on the abovementioned precious metal catalysts, particularly on palladium-on-charcoal, for 2 to 8 hours. After separating off the catalyst and distilling off the solvent, the dialkylamino compound of the formula (1) is obtained in high yield and purity.

The identity of the compounds prepared according to this process is ensured by $^1H$ and $^{13}C$ NMR spectra.

EXAMPLE 1

68.5 parts of p-cresidine, 68.5 parts of toluene and 5 parts of catalyst (5% palladium/charcoal) are initially introduced into an autoclave. The autoclave is sealed and rinsed with nitrogen. 132 parts of acetaldehyde are then added in one portion by means of a pressure transfer-tube. The reductive alkylation is carried out over 3 hours at 100° C. and 40 to 60 bar hydrogen pressure. The catalyst is then filtered off and the volatile components distilled off under reduced pressure. 99 parts of crude N,N-diethylamino-p-cresyl methyl ether (purity: 89.5%) (HPLC)), ie. 92.7% of theory, are obtained.

Comparable results regarding yield and purity are obtained when toluene is replaced by xylene, methyl glycol, ethyl acetate or butanol.

EXAMPLE 2

A solution of 83.5 parts of 3-nitro-4-methoxytoluene in 352 parts of n-butyl acetate is initially introduced into an autoclave and 5 parts of triethylamine and 5 parts of catalyst (5% palladium/charcoal) are added. The autoclave is sealed and flushed with nitrogen. 132 parts of acetaldehyde are then added in one portion by means of a pressure transfer-tube. The reductive alkylation is carried out over 2 hours at 100° C. and 40 to 60 bar hydrogen pressure. The catalyst is then filtered off under suction and the volatile components distilled off under reduced pressure. 99 parts of crude N,N-diethylamino-p-cresyl methyl ether (purity: 90.8% (HPLC)), ie. 93.2% of theory, are obtained.

EXAMPLE 3

76.5 parts of aminohydroquinone dimethyl ether, 76.5 parts of ethanol, 5 parts of triethylamine and 5 parts of catalyst (5% palladium/charcoal) are initially introduced into an autoclave. The autoclave is sealed and flushed with nitrogen. 110 parts of acetaldehyde are then added in one portion by means of a pressure transfer-tube. The reductive alkylation is carried out over 2 hours at 100° C. and 40 to 60 bar hydrogen pressure. The catalyst is then filtered off and the volatile components distilled off under reduced pressure. 105.6 parts of crude N,N-diethylaminohydroquinone dimethyl ether (purity: 89.9% (HPLC)), ie. 90.8% of theory, remain.

EXAMPLE 4

A solution of 83.5 parts of 4-nitrobenzoic acid in 334 parts of n-butyl acetate is initially introduced into an autoclave and 5 parts of triethylamine and 5 parts of catalyst (5% palladium/charcoal) are added. The autoclave is sealed and flushed with nitrogen. 132 parts of acetaldehyde are then added in one portion by means of a pressure transfer-tube. The reductive alkylation is carried out over 2 hours at 100° C. and 40 to 60 bar hydrogen pressure. The catalyst is then filtered off and the volatile components distilled off under reduced pressure. 100 parts of crude 4-N,N-diethylaminobenzoic acid (purity: 74.0% (HPLC)), ie. 76.7% of theory, are obtained.

The target product is obtained in comparable yield and quality if the butyl acetate is replaced by glycol diacetate and the remaining process is carried out in the same fashion.

EXAMPLE 5

A solution of 52.5 parts of 2-nitro-4-acetaminoanisole in 210 parts of n-butyl acetate is initially introduced into an autoclave and 2.5 parts of triethylamine and 2.5 parts of catalyst (5% palladium/charcoal) are added. The autoclave is sealed and flushed with nitrogen. 66 parts of acetaldehyde are then added in one portion by means of a pressure transfer-tube. The reductive alkylation is carried out over 2 hours at 100° C. and 40 to 60 bar hydrogen pressure. The catalyst is then filtered off and the volatile components are distilled off under reduced pressure. 64.1 parts of crude 2-diethylamino-4-acetaminoanisole (purity: 88.5% (HPLC)), ie. 92.9% of theory, remain.

EXAMPLE 6

A solution of 18.3 parts of nitrohydroquinone dimethyl ether in 164.7 parts of xylene is initially introduced into an autoclave and 58 parts of propionaldehyde and 1 part of catalyst (5% palladium/charcoal) are added. The autoclave is sealed and flushed with nitrogen. The reductive alkylation is carried out over 3 hours at 100° C. and 40 to 60 bar hydrogen pressure. The catalyst is then filtered off and the volatile components distilled off under reduced pressure. 25 parts of crude N,N-di-n-propylaminohydroquinone dimethyl ether (purity: 91.0% (HPLC)), ie. 96.0% of theory, are obtained.

A comparable result is obtained if the palladium catalyst is replaced by the same amount of platinum/BaSO$_4$ and the remaining process is carried out as stated.

EXAMPLE 7

A solution of 76.5 parts of m-nitroanisole in 306 parts of n-butyl acetate is initially introduced into an autoclave and 5 parts of triethylamine and 5 parts of catalyst (5% palladium/charcoal) are added. The autoclave is sealed and flushed with nitrogen. 132 parts of acetaldehyde are then added in one portion by means of a pressure transfer-tube. The reductive alkylation is carried out over 3 hours at 100° C. and 40 to 60 bar hydrogen pressure. The catalyst is then filtered off and the volatile components distilled off under reduced pressure. 89.1 parts of crude N,N-diethyl-m-anisidine (purity: 92.5% (HPLC)), ie. 78.1% of theory, remain.

EXAMPLE 8

89 parts of 3-amino-butyranilide, 89 parts of n-butyl acetate, 5 parts of triethylamine and 5 parts of catalyst (5% palladium/charcoal) are initially introduced into an autoclave. The autoclave is sealed and flushed with nitrogen. 132 parts of acetaldehyde are then added in one portion by means of a pressure transfer-tube. The reductive alkylation is carried out over 2 hours at 70° to 80° C. and 40 to 60 bar hydrogen pressure. The catalyst is then filtered off and the volatile components distilled off under reduced pressure. 115.4 parts of crude 3-N,N-diethylaminobutyranilide (purity: 91.2% (HPLC)), ie. 90% of theory, are obtained.

EXAMPLE 9

A solution of 18.3 parts of nitrohydroquinone dimethyl ether in 164.7 parts of n-butyl acetate is initially introduced into an autoclave and 72 parts of n-butyraldehyde and 1 part of catalyst (5% palladium/charcoal) are added. The autoclave is sealed and flushed with nitrogen. The reductive alkylation is carried out over 3 hours at 100° C. and 40 to 60 bar hydrogen pressure. The catalyst is then filtered off and the volatile components distilled off under reduced pressure. 28 parts of crude N,N-di-n-butylaminohydroquinone dimethyl ether (purity: 86.1% (HPLC)), ie. 91.0% of theory, are obtained.

EXAMPLE 10

A solution of 91.5 parts of nitrohydroquinone dimethyl ether in 366 parts of n-butyl acetate is initially introduced into an autoclave and 5 parts of catalyst (5% palladium/charcoal) are added. The autoclave is sealed and flushed with nitrogen. 154 parts of acetaldehyde are then added in one portion by means of a pressure transfer-tube. The reductive alkylation is carried out over 3 hours at 100° C. and 40 to 60 bar hydrogen pressure. The catalyst is then filtered off and the volatile components distilled off under reduced pressure. 105.8 parts of crude N,N-diethylaminohydroquinone dimethyl ether (purity: 96.0% (HPLC)), ie. 97.2% of theory, are obtained.

EXAMPLE 11

A solution of 90 parts of 3-nitroacetanilide in 270 parts of n-butyl acetate is initially introduced into an autoclave and 5 parts of catalyst (5% palladium/charcoal) are added. The autoclave is sealed and flushed with nitrogen. 154 parts of acetaldehyde are then added in one portion by means of a pressure transfer-tube. The reductive alkylation is carried out over 3 hours at 100° C. and 40 to 60 bar hydrogen pressure. The catalyst is then filtered off under suction and the volatile components distilled off under reduced pressure. 107.4 parts of crude 3-N,N-diethylaminoacetanilide (purity: 90.5% (HPLC)), ie. 94.4% of theory, remain.

EXAMPLE 12

A solution of 13.9 parts of o-nitrophenol in 125 parts of n-butyl acetate is initially introduced into an autoclave and 1 part of catalyst (5% palladium/charcoal) is added. The autoclave is sealed and flushed with nitrogen. 44 parts of acetaldehyde are then added in one portion by means of a pressure transfer-tube. The reductive alkylation is carried out over 4 hours at 100° C. and 40 to 60 bar hydrogen pressure. The catalyst is then filtered off and the volatile components distilled off under reduced pressure. 17.5 parts of crude 2-N,N-diethylaminophenol (purity: 78.8% (HPLC)), ie. 88.4% of theory, are obtained.

EXAMPLE 13

A solution of 57.8 parts of 3-nitrophenyl-ß-oxethylsulfone in 115 parts of n-butyl acetate is initially introduced into an autoclave and 2.5 parts of catalyst (5% palladium/charcoal) are added. The autoclave is sealed and flushed with nitrogen. 77 parts of acetaldehyde are then added in one portion by means of a pressure transfer-tube. The reductive alkylation is carried out over 4 hours at 100° C. and 40 to 60 bar hydrogen pressure. The catalyst is then filtered off and the volatile components distilled off under reduced pressure. 59.8 parts of crude 3-N,N-diethylaminophenyl-ß-oxethylsulfone (purity: 97.0% (HPLC)), ie. 90.3% of theory, are obtained.

EXAMPLE 14

A solution of 75.5 parts of 4-nitroethylbenzene in 302 parts of xylene is initially introduced into an autoclave and 5 parts of catalyst (5% palladium/charcoal) and 116 parts of propionaldehyde are added. The autoclave is sealed and flushed with nitrogen. The reductive alkylation is carried out over 4 hours at 100° C. and 40 to 60 bar hydrogen pressure. The catalyst is then filtered off and the volatile components distilled off under reduced pressure. 105 parts of crude 4-N,N-di-n-propylaminoethylbenzene (purity: 92.7% (HPLC)), ie. 95% of theory, are obtained.

EXAMPLE 15

A solution of 90.5 parts of 3-nitrophenyl n-propyl ether in 362 parts of n-butyl acetate is initially introduced into an autoclave and 5 parts of catalyst (5% palladium/charcoal) are added. The autoclave is sealed and flushed with nitrogen. 132 parts of acetaldehyde are then added in one portion by means of a pressure transfer-tube. The reductive alkylation is carried out over 4 hours at 100° C. and 40 to 60 bar hydrogen pressure. The catalyst is then filtered off and the volatile components distilled off under reduced pressure. 108 parts of crude 3-N,N-diethylaminophenyl n-propyl ether (purity: 89.5% (HPLC)), ie. 93.4% of theory, are obtained.

A comparable result is obtained if the palladium catalyst is replaced by a similar amount of $PtO_2$/charcoal and the remaining process is carried out in the same fashion.

EXAMPLE 16

A solution of 24.6 parts of nitrobenzene in 98.4 parts of n-butyl acetate is initially introduced into an autoclave and 100.8 parts of n-butyraldehyde and 2 parts of catalyst (5% palladium/charcoal) are added. The autoclave is sealed and flushed with nitrogen. The reductive alkylation is carried out over 3 hours at 100° C. and 40 to 60 bar hydrogen pressure. The catalyst is then filtered off under suction and the volatile components distilled off under reduced pressure. 43 parts of crude N,N-di-n-butylaniline (purity: 85.2% (HPLC)), ie. 89.7% of theory, are obtained.

EXAMPLE 17

A solution of 104 parts of n-propyl 4-nitrobenzoate in 418 parts of n-butyl acetate is initially introduced into an autoclave and 174 parts of propionaldehyde and 5 parts of catalyst (5% palladium/charcoal) are added. The autoclave is sealed and flushed with nitrogen. The reductive alkylation is carried out over 3 hours at 100° C. and 40 to 60 bar hydrogen pressure. The catalyst is then filtered off and the volatile components distilled off under reduced pressure. 135 parts of crude n-propyl 4-N,N-di-npropylaminobenzoate (purity: 84.3% (HPLC)), ie. 86.5% of theory, are obtained.

EXAMPLE 18

A solution of 90.5 parts of 3-nitro-4-ethoxytoluene in 362 parts of n-butyl acetate is initially introduced into an autoclave and 5 parts of catalyst (5% palladium/charcoal) are added. The autoclave is sealed and flushed with nitrogen. 88 parts of acetaldehyde are then added in one portion by means of a pressure transfer-tube. The reductive alkylation is carried out over 2 hours at 100° C. and 40 to 60 bar hydrogen pressure. The catalyst is then filtered off and the volatile components distilled off under reduced pressure. 104 parts of crude N,N-diethylamino-p-cresyl ethyl ether (purity: 98.5% (HPLC)), ie. 90.0% of theory, are obtained.

EXAMPLE 19

A solution of 47.2 parts of m-nitrochlorobenzene in 425 parts of n-butyl acetate is initially introduced into an autoclave and 4.5 parts of catalyst (5% platinum/S/charcoal) are added. The autoclave is sealed and flushed with nitrogen. 44 parts of acetaldehyde are then added in one portion by means of a pressure transfer-tube. The reductive alkylation is carried out over 5 hours at 100° C. and 40 to 60 bar hydrogen pressure. The catalyst is then filtered off and the volatile components distilled off under reduced pressure. 53 parts of crude 3-chloro-N,N-diethylaniline (purity: 92.5% (HPLC)), ie. 89.1% of theory, are obtained.

EXAMPLE 20

A solution of 40.4 parts of 3-nitrobenzenesulfonamide in 80.8 parts of dimethyl formamide is initially introduced into an autoclave and 4 parts of catalyst (5% palladium/charcoal) are added. The autoclave is sealed and flushed with nitrogen. 88 parts of acetaldehyde are then added in one portion by means of a pressure transfer-tube. The reductive alkylation is carried out over 6 hours at 140° C. and 40 to 60 bar hydrogen pressure. After filtering off the catalyst, the volatile components are distilled off under reduced pressure. 44 parts of crude N,N-diethylaminobenzenesulfonamide (purity: 88% (HPLC)), ie. 84.8% of theory, are obtained.

We claim:

1. A process for the preparation of aromatic dialkylamines of the formula (1)

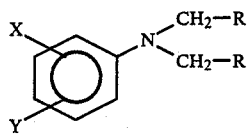 (1)

in which R denotes an alkyl-$C_1$-$C_6$ group, X and Y each denote a hydrogen, fluorine or chlorine atom or a hydroxyl, alkyl-$C_1$-$C_4$, alkoxy-$C_1$-$C_4$, carboxyl, carbalkoxy-$C_1$-$C_5$, alkyl-$C_1$-$C_4$-CO-NH-,

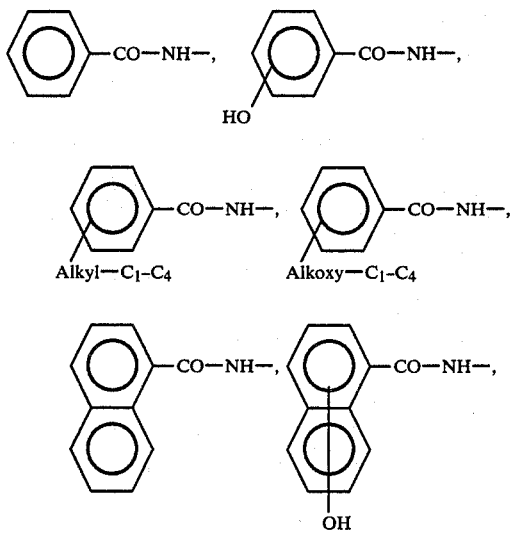

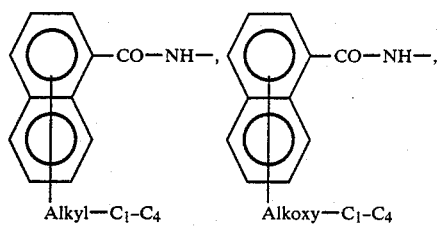

sulfonic acid, alkyl-$C_1$-$C_4$ sulfonate, sulfamoyl, alkyl-$C_1$-$C_4$-sulfonyl, hydroxy-alkylene-$C_1$-$C_4$ 14 sulfonyl, phenylsulfonyl, hydroxyphenylsulfonyl, alkyl-$C_1$-$C_4$-phenylsulfonyl or alkoxy-$C_7$-$C_4$-phenylsulfonyl group, wherein compounds of the formula (2)

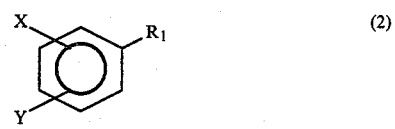 (2)

In which $R_1$ denotes a nitro or primary amino group, and X and Y have the abovementioned meanings, are reductively dialkylated, said process comprising: carrying out the reductive dialkylation selectively, with a yield of greater than 70% di-alkylated product of formula (1), by reacting a compound of formula (2) with at least an equimolar amount of an aldehyde of the formula (3)

 (3)

in which R has the abovementined meaning, in a non-acid reaction medium comprising an alcohol, an alkylbenzene, a glycol ether, a fatty acid dialkylamide or fatty acid alky ester or fatty acid glycol ester, and using catalytically activated hydrogen in the presence of a catalyst consisting essentially of palladium, platinum, platinum dioxide or sulfided or sulfited platinum, at temperatures from 50° C. to 150° C. at a pressure from 20 bar to 100 bar.

2. The process as claimed in claim 1, wherein the reductive dialkylation is carried out in the presence of a catalytic amount of a trialkyl-$C_1$-to-$C_6$14 amine.

3. The process as claimed in claim 1, wherein the reductive dialkylation is carried out at temperatures from 80° C. to 120° C. and at a pressure of 40 bar to 60 bar.

4. The process as claimed in claim 1, wherein the process is carried out in a basic medium.

5. The process as claimed in claim 1, wherein the catalyst consists essentially of palladium on carbon.

* * * * *

UNITED STATES PATENT AND TRADEMARK OFFICE
CERTIFICATE OF CORRECTION

PATENT NO. : 4,760,183
DATED : July 26, 1988
INVENTOR(S) : Theodor Papenfuhs and Walter Kuhn It is certified that error appears in the above-identified patent and that said Letters Patent is hereby corrected as shown below:

at column 10, line 14, the number "14" should be eliminated, at column 10, at line 25, "In" should read --in--, at column 10, at line 38, "abovementined" should read --abovementioned--.

Signed and Sealed this

Seventeenth Day of January, 1989

Attest:

DONALD J. QUIGG

Attesting Officer

Commissioner of Patents and Trademarks